United States Patent [19]

Maucher

[11] 4,386,527

[45] Jun. 7, 1983

[54] ULTRASONIC MEASURING INSTRUMENT

[75] Inventor: Charles Maucher, Newark, Del.

[73] Assignee: E. I. Du Pont de Nemours and Company, Wilmington, Del.

[21] Appl. No.: 260,194

[22] Filed: May 4, 1981

[51] Int. Cl.³ .............................................. G01N 29/04
[52] U.S. Cl. ........................................ 73/597; 73/622
[58] Field of Search .................. 73/597, 622, 637, 638

[56] References Cited

U.S. PATENT DOCUMENTS

| 2,932,818 | 4/1960 | Lubkin | 340/244 |
| 2,966,057 | 12/1960 | Heller | 73/67.6 |
| 3,229,508 | 1/1966 | Sharpe et al. | 73/67.5 |
| 3,427,867 | 2/1969 | Nute et al. | 73/67.9 |

Primary Examiner—Howard A. Birmiel

[57] ABSTRACT

An instrument for distinguishing between gray and ductile cast iron pipes. Signals from a relatively movable pair of ultrasonic probes and a distance transducer are inputs to a circuit for generating a signal related to the velocity of sound through a chord of a pipe.

3 Claims, 5 Drawing Figures

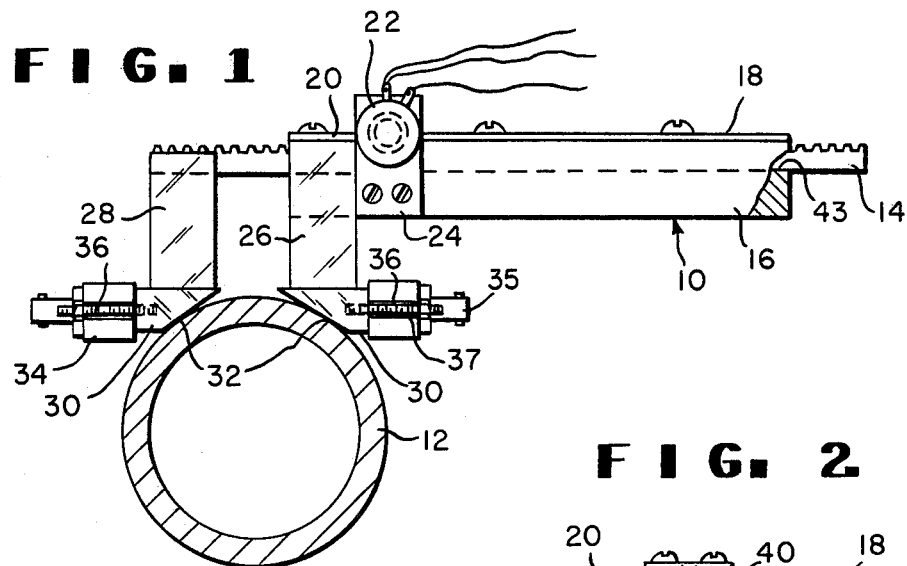
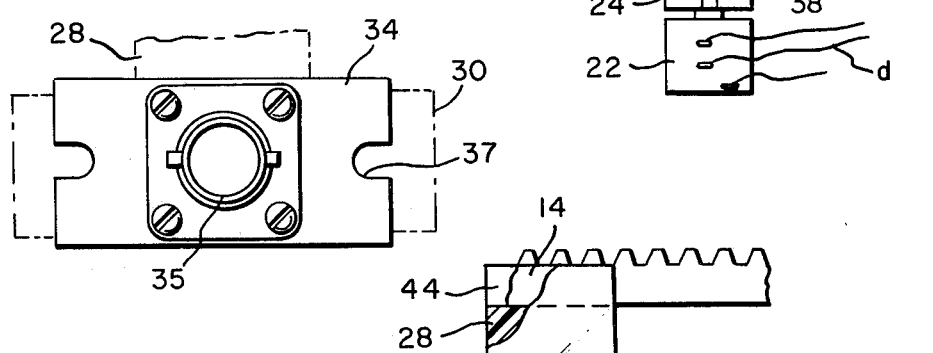
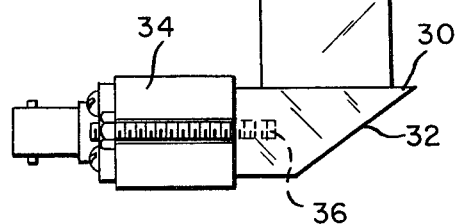

ULTRASONIC MEASURING INSTRUMENT

BACKGROUND

This invention relates, generally, to the identification of materials and, more particularly, to the classification of structurally similar objects according to the materials of construction.

In the operation of plants where corrosive materials such as sulfuric acid are used or made, it is necessary to determine the extent of corrosion in transfer pipes and this is often accomplished by ultrasonic thickness measurements. Before making such a measurement, it is first necessary to know the material of the pipe, for example, in the case of a transfer pipe for sulfuric acid, whether the pipe is gray or ductile cast iron. Both types are found in the plants as well as in stock piles from which replacement lengths are selected. In these and other instances, there is a need for portable equipment with which pipes and similar objects can be identified quickly and positively.

SUMMRY OF INVENTION

The needs identified above have been met with a portable, ultrasonic instrument that has a pair of relatively movable probes and a potentiometer operatively connected to both probes. The potentiometer and the probes are connected to an electrical circuit that includes a component for generating a velocity signal based on the spacing of the probes and the elapsed time for transmission of vibrations through an object located between the probes.

DESCRIPTION OF DRAWINGS

In the following description of the invention, reference is made to the accompanying drawings wherein:

FIG. 1 is an elevational view of the instrument positioned with respect to a pipe;

FIGS. 2-4 are fragmentary top, elevational and end views, respectively; and

DESCRIPTION OF INVENTION

Figure 5:
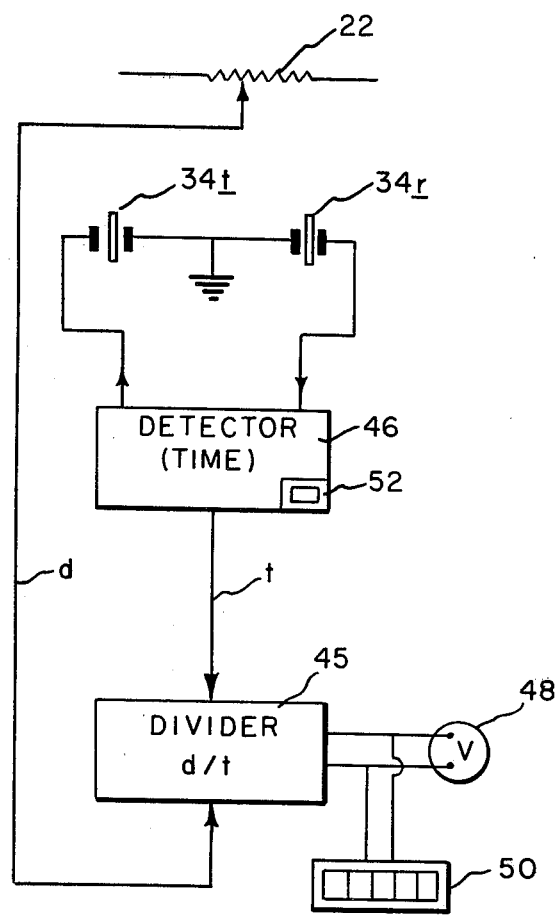
FIG. 5 is a schematic view of the instrument and associated circuitry.

In FIG. 1, a portable, ultrasonic instrument 10 has been shown in position on a pipe 12. The instrument includes an elongated rack 14 on which a support housing 16 is slidably mounted. Rack 14 is retained in a channel in housing 16 by a pair of plates 18, 20 and is coupled to a distance sensor 22 which, in this instance, is a rotary potentiometer. Potentiometer 22 is carried by a mounting bracket 24.

Closely adjacent bracket 24, a plastic mounting block 26 is fixed to support housing 16 by an adhesive. Block 26 is channeled to receive housing 16. Another mounting block 28 is similarly fixed to rack 14. Each mounting block carries a shoe 30 made from a Lucite® acrylic resin. At one end, each shoe 30 has an angularly disposed surface 32 adapted to engage pipe 12. At its other end, each shoe carries an ultrasonic transducer or probe 34. The probes 34 are equidistant from rack 14. One probe is a transmitter, the other a receiver of ultrasonic vibrations.

In an operable embodiment, the probes 34 are commercially available, ultrasonic, shear-wave transducers (NORTEK, Model ZL-Z-¼×1-2.25). Potentiometer 22 is a precision, 10-turn potentiometer (Spectrol, Model 534) having independent linearity. Each probe 34 includes a piezo-electric crystal and thin conductive electrodes sandwiched between plastic plates in a metal case and is equipped with an electrical connector 35. The operational frequency of the crystals is 2.25 megahertz (MHz). Each probe is attached to a shoe 30 by screws 36 located in grooves 37 in the metal case.

Further details and structural arrangements of various parts mentioned above are shown in FIGS. 2-4. In FIG. 2, potentiometer 22 is shown with a shaft 38 that extends through bracket 24 to a second bracket 40 on the opposite side of support housing 16. On shaft 38, there is a pinion 42 that meshes with the teeth on rack 14. Rack 14 is retained in a channel 43 in housing 16 by plates 18, 20. As shown in FIG. 3, rack 14 fits in a channel 44 in mounting block 28. In FIG. 4, the block 28 and a shoe 30 are shown in phantom behind a transducer 34 as an illustration of the relative widths of these parts.

Referring to FIG. 5, the output of the potentiometer 22 is connected to a circuit component 45 for generating a velocity signal. The other input to component 45 is from a detection unit 46 having one switch position at which contained circuitry for the measurement of elapsed time for the transmission of sound energy between the probes 34 is energized. That circuitry includes a source of oscillations for the transmitting probe 34$t$ and receives a corresponding input from the receiving probe 34$r$. The component 45 generates a signal related to the velocity of transmission and displays it on a voltmeter 48 and/or a digital read-out device 50.

In the operable embodiment, the component 45 is an analog divider in the form of a sealed semiconductor (Analog Devices, Model 434) and the detection unit 46 is a commercially available, portable, test instrument (Krautkramer-Branson, Model ULS-38).

In operation, the shoes 30 are positioned in acoustic contact with a pipe 12, with the probes 34 across a chord. High frequency pulses are transmitted from probe 34$t$ to probe 34$r$ and a time-related signal is generated in detection unit 46. That signal t and signal d from the potentiometer 22 are processed in the divider 45 and a velocity-related signal V is displayed on the voltmeter 48 and/or the digital readout device 50. Either of these displays tells an operator which species of pipe is being inspected, the velocities through gray and ductile pipes being different and having been determined in advance. Thus, this nondestructive test eliminates the possibility of erroneous selections of pipe from stock. In the case of existing installations, portability of the instrument facilitates quick and positive identifications. Once an installed pipe has been identified, a thickness probe can be plugged into the detection unit 46 and that unit can be switched to measure and display thickness on a scope 52 instead of transmitting time signal t to divider 45. Thus, the possibility of being misled by a thickness measurement of a gray iron pipe thought to be ductile, and vice-versa, is avoided.

The instrument is also useful in distinguishing between steel bars and plates that have and have not been heat treated. Other objects that can be identified and/or distinguished will occur to those skilled in the art.

What is claimed as new and desired to be secured by Letters Patent is:

1. A portable instrument comprising:
   an elongated support;
   a first ultrasonic transducer fixed mounted with respect to said support;

a second ultrasonic transducer slidably mounted with respect to said support;

a potentiometer operably connected between the transducers for generating a signal dependent on the distance therebetween;

first circuitry connected to the transducers for generating a signal related to the elapsed time for transmission of sound energy through an object located between the transducers; and second circuitry connected to the first circuitry and said potentiometer for generating a signal representative of the velocity of the sound energy, said velocity signal being based on the distance between said transducers and the output of said first circuitry.

2. The instrument of claim 1 wherein is provided a pair of plastic shoes, each having an angularly disposed surface adapted to bear against a round object and carrying one of the transducers, one shoe being fixedly mounted, the other for sliding movement with respect to said support.

3. The instrument of claim 1 wherein said potentiometer is a rotary potentiometer and wherein is provided a rack-and-pinion coupling between the support and potentiometer.

* * * * *